(12) United States Patent
Chen et al.

(10) Patent No.: US 12,180,629 B2
(45) Date of Patent: Dec. 31, 2024

(54) HIGHLY ALIGNED AND PACKED HOLLOW FIBER ASSEMBLY

(71) Applicant: MTAMTECH INC., Taipei (TW)

(72) Inventors: Chien Chung Chen, Taipei (TW); Chee Ho Chew, New Taipei (TW); Wan Ting Huang, Taipei (TW)

(73) Assignee: MTAMTECH INC., Taipei (TW)

( * ) Notice: Subject to any disclaimer, the term of this patent is extended or adjusted under 35 U.S.C. 154(b) by 239 days.

(21) Appl. No.: 17/600,030

(22) PCT Filed: Mar. 30, 2020

(86) PCT No.: PCT/CN2020/082184
§ 371 (c)(1),
(2) Date: Sep. 29, 2021

(87) PCT Pub. No.: WO2020/200179
PCT Pub. Date: Oct. 8, 2020

(65) Prior Publication Data
US 2022/0186416 A1    Jun. 16, 2022

Related U.S. Application Data

(60) Provisional application No. 62/826,701, filed on Mar. 29, 2019.

(51) Int. Cl.
| | |
|---|---|
| *D04H 1/728* | (2012.01) |
| *B01D 69/08* | (2006.01) |
| *D01D 5/00* | (2006.01) |
| *D01D 5/24* | (2006.01) |
| *D01D 5/34* | (2006.01) |

(52) U.S. Cl.
CPC ............ *D04H 1/728* (2013.01); *B01D 69/08* (2013.01); *D01D 5/0007* (2013.01); *D01D 5/24* (2013.01); *D01D 5/34* (2013.01); *D10B 2505/04* (2013.01)

(58) Field of Classification Search
None
See application file for complete search history.

(56) References Cited

U.S. PATENT DOCUMENTS

| | | | |
|---|---|---|---|
| 2011/0264235 A1 | 10/2011 | Chen et al. | |
| 2013/0112618 A1* | 5/2013 | Diallo | B01D 69/12 210/500.33 |
| 2014/0162521 A1* | 6/2014 | Chen | D01D 5/0061 442/338 |

FOREIGN PATENT DOCUMENTS

| | | |
|---|---|---|
| CN | 102534836 A | 7/2012 |
| CN | 106232215 A | 12/2016 |
| TW | 201137195 A | 11/2011 |

OTHER PUBLICATIONS

English Abstract for Taiwan Publication No. TW201422399A, downloaded from the European Patent Office on Oct. 28, 2021.
(Continued)

*Primary Examiner* — Shawn Mckinnon
(74) *Attorney, Agent, or Firm* — Prosyla Group PC

(57) ABSTRACT

The invention relates to a highly aligned and closely packed electrospun fiber assembly, wherein the fibers have at least an extension part or pore on the surface thereof. The invention also relates to a microtube array membrane (MTAM), comprising fiber assembly of the present disclosure. The invention also relates to the applications of these electrospun fiber assemblies in biological applications, and method of manufacturing these electrospun fiber assemblies.

17 Claims, 9 Drawing Sheets

(56) References Cited

OTHER PUBLICATIONS

English Translation of Search Report dated Nov. 17, , issued in Taiwan Application No. 109110904.
Notice of Allowance issued on Jun. 15, 2021, in Taiwan Application No. 109110904.
Office Action dated Nov. 18, 2020, in Taiwan Application No. 109110904.
Patent Gazette Certificate No. TWI7437258 issued on Oct. 21, 2021 for Taiwan Application No. 109110904.
First Office Action issued in China Patent Application No. 202080026526.0 dated Jul. 5, 2022. (Chinese application has issued as Patent No. CN 113677837 A.).
Second Office Action issued in Chinese Patent Application No. 202080026526.0 dated Mar. 10, 2023. (Chinese application has since issued as Patent No. CN 113677837 A.).
First Examination Report received in Indian Patent Application No. 202127044639 dated Jul. 31, 2023.

\* cited by examiner (a)

(b)

(a)

(b)

HIGHLY ALIGNED AND PACKED HOLLOW FIBER ASSEMBLY

PRIORITY DATA

This application is a 371 National Phase of International Patent Application No. PCT/CN2020/082184, filed Mar. 30, 2020, which claims priority to and benefit of Priority Patent Application No. 62/826,701, filed Mar. 29, 2019, the contents of which is incorporated by reference in its entirety.

FIELD OF THE INVENTION

The present disclosure relates to electrospun fiber and fiber array with nanoscale hairy, double layer or alternative layer structure.

BACKGROUND OF THE INVENTION

Electrospinning is an established technique used to produce non-woven fiber mats for a variety of applications, such as drug delivery vehicles, tissue engineering scaffolds, nanofiltration membranes, and battery materials. Electrospinning is a process that relies on electric charges to deform a conical droplet of polymeric solution ejected from a nozzle tip into ultra-fine fibers. Electrospinning makes it relatively easy to spin continuous nanofibers from many different materials, including, but not limited to, polymers. Electrospinning provides a straightforward and practical way to produce fibers with diameters ranging from a few to about two-thousand nanometers. Electrospinning represents a versatile, low-cost method for producing micron- to nano-scale fibers in the form of either membrane or 3-D structure.

WO 2005095684 is directed to substantially continuous fibers which have a core-and-shell structure; however, these fibers are randomly arranged, not aligned and packed. U.S. Pat. No. 9,713,521B2 relates to a highly aligned and closely packed fiber assembly, wherein at least 5 fibers are packed together, and the orientation of the fibers is no larger than +/−5°, and its preparation and applications. US 20180100249 provides polymer nanofiber or microfiber mats or membranes and methods for their preparation via an aqueous, one-step polyelectrolyte complexation and electrospinning of complex coacervates.

However, there is still a need to improve surface-to-volume ratios, specific surface area, or porosity of electrospun fibers.

SUMMARY OF THE INVENTION

The present disclosure provides a hollow electrospun fiber assembly, comprising multiple fibers having nanoscale hair like structures extended from inner surface thereof.

In one embodiment, the hairy like structure of the fiber has a length ranging from about 100 nm to about 1 µm. In some further embodiments, the length of the hairy structure ranges from about 200 nm to about 1 µm, about 300 nm to about 1 µm, about 400 nm to about 1 µm, about 500 nm to about 1 µm, about 600 nm to about 1 µm, about 700 nm to about 1 µm, about 800 nm to about 1 µm, about 900 nm to about 1 µm, about 200 nm to about 900 nm, about 200 nm to about 800 nm, about 200 nm to about 700 nm, about 200 nm to about 600 nm, about 200 nm to about 500 nm, about 200 nm to about 400 nm, about 200 nm to about 300 nm, about 300 nm to about 1 µm, about 300 nm to about 900 nm, about 300 nm to about 800 nm, about 300 nm to about 700 nm, about 300 nm to about 600 nm, about 300 nm to about 500 nm, about 300 nm to about 400 nm, about 400 nm to about 1 µm, about 400 nm to about 900 nm, about 400 nm to about 800 nm, about 400 nm to about 700 nm, about 400 nm to about 600 nm, about 500 nm to about 1 µm, about 500 nm to about 900 nm, about 500 nm to about 800 nm, about 500 nm to about 700 nm or about 500 nm to about 600 nm.

In one embodiment, the hairy like structure has an aspect ratio (or L/d ratio) of up to 20:1. In some embodiments, the hairy like structure has an aspect ratio of up to 15:1 or up to 10:1. In another embodiments, the hairy like structure has an aspect ratio of at least 1:1, at least 3:1 or at least 5:1. The aspect ratio is within a reasonable range with the above-mentioned end points. Certain embodiments of the aspect ratio include, but are not limited to, from 1:1 to 20:1, etc. In one embodiment, the surface coverage of the hair-like structure is about 10% to about 80%, about 10%/o to about 70%, about 10% to about 60%, about 10% to about 50%, about 10% to about 40%, about 10% to about 30%, about 20% to about 80%, about 20% to about 70%, about 20% to about 60%, about 20% to about 50%, about 30% to about 80%, about 30% to about 70%, about 30% to about 60%, about 40% to about 80%, about 40% to about 70%, about 50% to about 80%, or about 60% to about 80%.

In some embodiments, the pores on the surface of the fibers have a size ranging from about 5 nm to about 1 µm. In some embodiments, the pore size ranges from about 20 nm to about 500 nm, about 20 nm to about 400 nm, about 20 nm to about 300 nm, about 20 nm to about 200 nm, about 20 nm to about 100 nm, about 20 nm to about 80 nm, about 20 nm to about 70 nm or about 20 nm to about 60 nm. The density of the pores on the surface ranges from about 0.1% to about 30% In some embodiments, the density is from about 0.1% to about 25%, about 0.1% to about 20%, about 0.1% to about 15%, about 0.1% to about 10%, about 0.1% to about 5%, about 0.1% to about 15%, about 1% to about 30%, about 1% to about 25%, about 1% to about 20%, about 1% to about 15%, about 1% to about 10%, about 1% to about 5%, about 5% to about 30%, about 5% to about 25%, about 5% to about 20%, about 5% to about 15%, about 5% to about 10%, about 10% to about 30%, about 15% to about 25%, about or 15% to about 20%.

In one embodiment, the fiber has a core-shell structure. Embodiments of polymers used as core solution or shell solution include, but are not limited to, ethylene oxide, polyethylene oxide (PEO), ethylene glycol, polyethylene glycol (PEG), poly(lactic acid) (PLA), poly(glycolic acid) (PGA), nylon, polyesters, polyamides, poly(amic acids), polyimides, polyethers, polyketones, polyurethanes, polycaprolactones, polyacrylonitriles, polyaramides, conjugated polymers such as the electroluminescent polymer, poly(2-methoxy, 5 ethyl (2' hexyloxy) para-phenylene vinylene) (MEH-PPV), polyphenylenevinylenes, polyarylene-vinylenes, polythienolene-vinylenes, polypyrrolo-vinylenes, polyheteroarylene-vinylenes, polyanilines, polyphenylenes, polyarylenes, polythiophenes, polypyrroles, polyheteroarylenes, polyphenylene-ethynylenes, polyarylene-ethynylenes, polythieno-ethynylenes, polyheteroarylene-ethynylenes, and mixtures thereof. In some embodiments, the polymer is a biodegradable and/or bioabsorbable polymer such as polyglycolide (PGA) and its random copolymer poly(glycolide-co-lactide) (PGA-co-PLA), polyhydroxyalkyl methacrylates including ethylmethacrylate, and hydrogels such as polyvinylpyrrolidone, polyacrylamides, collagen, gelatin, alginic acid, chitin, chitosan, fibrin, hyaluronic acid, dextran and polyamino acids, or a mixture thereof. In a further embodiment, the solution is a mixture of PLA, PEO and PEG. In one embodiment, the core is composed of a mixture of PLA, PEO and PEG.

In one embodiment, at least five (5) fibers in the fiber assembly are packed together; preferably, at least 20 fibers; more preferably, at least 50 fibers; and most preferably, at least 100 or 200 fibers are packed together. In further embodiments, the number of the fibers packed together in the fiber assembly ranges from 5 to 200, 20 to 200, 10 to 200, 20 to 200, 20 to 100, 50 to 200 or 50 to 100. In one embodiment, the fiber assembly is in a form of film, membrane, or sheet. In another embodiment, fiber assembly has a concentric appearance.

In another embodiment, the fiber orientation in the assembly is no larger than +/−5°; preferably, no larger than +/−4°; more preferably, no larger than +/−2°; most preferably, no larger than +/−1°. In one further embodiment, the fiber orientation in the assembly is about +/−1° to about +/−5°, and more preferably, about +/−1° to about +/−4°.

According to another embodiment of the invention, the length-to-diameter (outer) ratio (L/d) of the fiber is larger than about 20. Preferably, the L/d is larger than about 1,00, more preferably, larger than about 1,000, and most preferably, larger than about 10,000. In one embodiment of the invention, the L/d is about 20 to about 10,000. Preferably, the ratio is about to 1,000, and more preferably, about 20 to about 100.

The present disclosure also provides a microtube array membrane (MTAM) comprising one or more layers of hollow electrospinning fiber assembly as described herein.

In one embodiment, the MTAM comprises at least two layers of the fiber assembly. In a further embodiment, MTAM has a structure wherein the layers of fibers are alternatively or perpendicularly arranged.

The present disclosure also provides a pocket enclosing the MTMAs described herein.

The present disclosure also provides a method of using a hollow electrospun fiber assembly or MTAM of the present disclosure in drug screening, matrix form cell cultivation, fermentation, tissue engineering, drug screening (such as cancer drug screening and cancer immunotherapeutic drug screening) and filtration (such as dialysis).

DETAILED DESCRIPTION OF THE INVENTION

Figure 1:
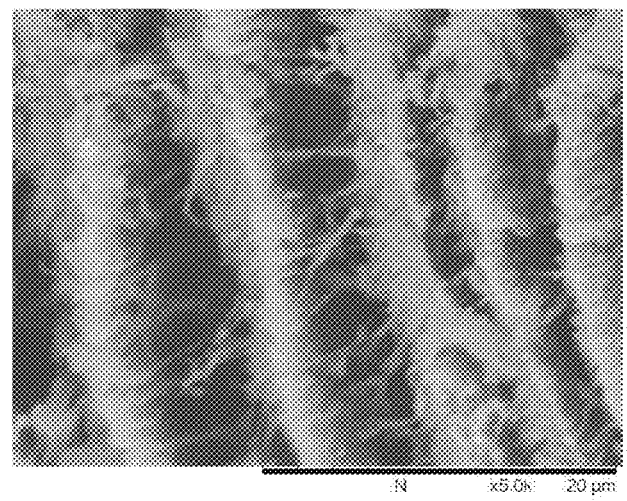
FIG. 1 shows SEM images (transverse view) of embodiments of MTAM-h (having hairy extension parts).

Although many of the words, terms and titles employed herein are commonly used and conventionally understood within traditional medical and scientific contexts, summary descriptions and definitions of some terms and of particular names, designations, epithets or appellations are provided below. These descriptions and definitions are provided as an aid in recognizing and appreciating the true variety and range of applications intended for inclusion within the scope of the present methodology.

As used herein, the term "microtube array membrane" (abbreviated as "MTMA") refers to a film or membrane consisting of one or more layers of oriented hollow nano-sized fibers. A suffix appended to the term "MTMA" refers to a specific configuration of arrays or surface morphology of the fibers, while a prefix appended to the term "MTMA" refers to the materials thereof. For example, "MTMA-Hairy" means that the fibers of the microtube array membrane have hairy extension parts on the surface of the fibers; "MTMA-al" means that the layers of fibers are arranged alternatively in the z-direction; "PLLA-MTMA" means a microtube array membrane consisting of polylactic acid, etc.

As used herein, the term "electrospinning" refers to a technology which produces nano-sized fibers referred to as electrospun fibers from a solution using interactions between fluid dynamics and charged surfaces. In general, formation of the electrospun fiber involves providing a solution to an orifice in a body in electric communication with a voltage source, wherein electric forces assist in forming fine fibers that are deposited on a surface that may be grounded or otherwise at a lower voltage than the body. In electrospinning, a polymeric solution or melt provided from one or more needles, slots or other orifices is charged to a high voltage relative to a collection grid. Electrical forces overcome surface tension and cause a fine jet of the polymeric solution or melt to move towards the grounded or oppositely charged collection grid.

As used herein, the term "polymer" refers to and generally includes, but is not limited to, homopolymers, copolymers, such as, for example, block, graft, random and alternating copolymers, terpolymers, etc. and blends and modifications thereof. Preferably, it can include, but are not limited to, polyalkyene oxide (e.g., PEO, PPO, PEO/PPO, etc.), polylactides, polylactic acids, polyolefins, polyacrylonitrile, polyurethane, polycarbonate, polycaprolactone, polyvinyl alcohol (PVA), cellulose, chitosan nylon (e.g., nylon 6, nylon 406, nylon 6-6, etc.), polystyrene, proteins, and the like, or combinations thereof. Unless otherwise specifically limited, the term "polymer" is intended to include all possible geometrical configurations of the material. These configurations include, but are not limited to, isotactic, syndiotactic and random symmetries. Suitable solvents for each polymer can be selected from solvents known to those skilled in the art, including, but not limited to, sulfuric acid, formic acid, chloroform, tetrahydrofuran, dimethyl formamide, water, acetone, and combinations thereof.

As used herein, the term "nano-sized fibers" or "nanofibers" refers to very small diameter fibers having an average diameter not greater than about 1500 nanometers (nm). Nanofibers are generally understood to have a fiber diameter range of about 10 to about 1500 nm, more specifically about 10 to about 1000 nm, more specifically still about 20 to about 500 nm, and most specifically about 20 to about 400 nm. Other exemplary ranges include about 50 to about 500 nm, about 100 to 500 nm, or about 40 to about 200 nm. In instances where particulates are present and heterogeneously distributed on nanofibers, the average diameter of a nanofiber can be measured using known techniques (e.g., image analysis tools coupled with electro microscopy), but excluding the portions of a fiber that are substantially enlarged by the presence of added particles relative to the particle free portions of the fiber.

As used herein, the term "oriented fibers" indicates that substantially all fibers in a specific structure or array are arranged parallel to each other in a longitudinal direction ("unidirectionally oriented") or in a well-defined three-dimensional network ("three-dimensionally oriented"). In other words, the fibers are not randomly spatially arranged with respect to each other. In most instances, the fibers described herein grow in a generally perpendicular direction relative to the supporting substrate surface and there is very minimal, if any, branching of individual fiber strands.

As used herein, the term "single layer of material" or "single-layered material" refers to a material composed of a single layer which can be variable in thickness.

As used herein, the term "plurality of layers" or "multi-layered material" refers to a "stack" of single-layered materials.

As used herein, the term "hair-like" or "hairy" is used for describing the appearance of the extension parts from the surface of the fibers, or the appearance of the entirety of the extension parts. A "hair-like" or "hairy" shape involves at least one filament, string, thread, fibril, hair, etc., consisting of the material of the fibers and connecting to the surface of the fibers.

The invention unexpected found that creation of hair like structure within the lumen of electrospun fibers increases surface areas of the fibers and allows the fibers scalable easily. Accordingly, the present disclosure provides hollow electrospun fibers, fiber assembly having large surface-to-volume ratios, high specific surface area, or interconnected porosity and microtube array membrane (MTAM) comprising one or multiple layers of the fiber assembly. The electrospun fibers, fiber assembly and MTAM have high specific surface ratio and thus can be used in various applications such as drug screening, matrix form cell cultivation, fermentation, tissue engineering, drug screening (such as cancer drug screening and cancer immunotherapeutic drug screening) and filtration (such as dialysis).

Hollow Electrospinning Fiber Assembly Having Fibers Having Nanoscale Hair Like Structures The fibers of the hollow electrospinning fiber assembly and the MTAM have a hairy like structure which extends from inner surface of the fibers. The hair like structure grows from the inner surface of the fibers. The surface coverage ratio of the hair-like structure is about 10% to about 80%, about 10% to about 70%, about 10% to about 60%, about 10% to about 50%, about 10% to about 40%, about 10% to about 30%, about 20% to about 80%, about 20% to about 70%, about 20% to about 60%, about 20% to about 50%, about 30% to about 80%, about 30% to about 70%, about 30% to about 60%, about 40% to about 80%, about 40% to about 70%, about 50% to about 80%, or about 60% to about 80%. The surface coverage ratio can be estimated based on the SEM images. The hairy like structure in the fibers provide larger surface area and are easily scalable so that less fibers are needed for use in various applications and thus the cost can be reduced. In addition, the "hair" may have an aspect ratio of up to 20:1. Embodiments of the aspect ratio of the hairy like structure include, but are not limited to, up to 15:1, up to 10:1, at least 1:1, at least 3:1 or at least 5:1, from 1:1 to 20:1.

The fibers are hollow and have pores on the inner surface. In one embodiment, the fibers are hollow and have pores on both inner and outer surfaces. Having pores on the surface(s) of the fibers, the fiber assembly is deemed having a "sponge-like" appearance. In certain embodiments, the thickness of the fiber ranges from 1 to 5 μm, e.g., from 1.5 to 4 μm, from 2 to 3 μm, etc.

In the electrospinning process, the formation of the electrospun fibers can be divided into three stages (1) Taylor cone (2) stable jet and (3) instable jet stage (Polym Int 56:1361-1366, 2007). Coaxial electrospinning also can be used to electrospin a first polymeric solution as a shell around a second polymeric solution as a core. Through this process, polymeric solutions are delivered through a co-axial spinneret. The fibers can be produced using the method disclosed in US 20150342719A1, which is entirely incorporated by reference.

The present disclosure also provides a method of preparing the fibers with nanoscale 1s hair like structures, comprising in a two-fluid coxial electrospinning process, using a polymeric core solution comprising about 5 wt % to about 40 wt % polymeric solution dissolved in a solvent at a ratio of about 7:about 2 to about 9:about 1; and a polymeric shell solution comprising about 5 wt % to about 40 wt % polymeric solution dissolved in a solvent at a ratio of about 7:about 2 to about 9:about 1. In one embodiment, the solvent is a co-solvent of dichloromethane:dimethylformaldehyde (DCM:DMF).

Embodiments of polymers used as core solution or shell solution include, but are not limited to, ethylene oxide, polyethylene oxide (PEO), ethylene glycol, polyethylene glycol (PEG), poly(lactic acid) (PLA), poly(glycolic acid) (PGA), nylon, polyesters, polyamides, poly(amic acids), polyimides, polyethers, polyketones, polyurethanes, polycaprolactones, polyacrylonitriles, polyaramides, conjugated polymers such as the electroluminescent polymer, poly(2-methoxy, 5 ethyl (2' hexyloxy) para-phenylene vinylene) (MEH-PPV), polyphenylenevinylenes, polyarylene-vinylenes, polythienolene-vinylenes, polypyrrolo-vinylenes, polyheteroarylene-vinylenes, polyanilines, polyphenylenes, polyarylenes, polythiophenes, polypyrroles, polyheteroarylenes, polyphenylene-ethynylenes, polyarylene-ethynylenes, polythieno-ethynylenes, polyheteroarylene-ethynylenes, and mixtures thereof. In some embodiments, the polymer is a biodegradable and/or bioabsorbable polymer such as polyglycolide (PGA) and its random copolymer poly(glycolide-co-lactide) (PGA-co-PLA), polyhydroxyalkyl methacrylates including ethylmethacrylate, and hydrogels such as polyvinylpyrrolidone, polyacrylamides, collagen, gelatin, alginic acid, chitin, chitosan, fibrin, hyaluronic acid, dextran and polyamino acids, or a mixture thereof. In a further embodiment, the solution is a mixture of PLA, PEO and PEG.

In a further embodiment, a flow rate of 3 to 10 mL (core solution) and 2 to 12 mL (shell solution) and/or about 80 to about 120 rpm of collection speed of the drum collector is used in the method of the present disclosure.

Microtube Array Membrane Having One or Multiple Layers of the Fiber Assembly

In another aspect, the present disclosure provides a microtube array membrane (MTAM), comprising one or more fiber assembly described herein.

In one embodiment, the MTAM has a structure wherein the layers of fiber assembly are alternatively arranged, called alternating layers. The term "alternatively" or "alternating layers" used herein means that layers of the fibers are stacked closely and are not completely aligned in the z-direction of the layers. For example, the layers of fibers in a two-layered membrane may have an "A-B" configuration when observed through the z-direction. For a three-layered membrane, the layers of fibers may have an "A-B-A" or "A-B-C" configuration when observed through the z-direction. The term "perpendicularly" or "perpendicular layers" used herein means that layers of the fibers are stacked closely and are completely aligned in the z-direction of the layers. These MTMAs are all expressed as "MTMA-al" but further suffices can be added to clearly specify the configuration and layer number of the MTMA. For example, MTMA having two layers arranged alternatively can be expressed as "MTMA-dl-al." In addition, MTMA-alternating layers may exhibit following characteristics or benefits: wastage of area minimized, higher packing density, potentially additional tubes can reduce intra system pressure, etc.

In another embodiment, the MTAM has a structure wherein the layers of fiber assembly are perpendicularly arranged, called perpendicular layers. That is, MTMA has the multiple layers of fibers which are aligned in the z-direction (the direction perpendicular to the membrane plane). For example, the MTMA having two layers of fibers aligned in the z-direction is expressed by "MTMA-dl"; the MTMA having three layers of fibers aligned in the z-direction is expressed by "MTMA-tl"; etc. MTMA having more layers of fibers can also be provided. MTMA-perpendicular layers may exhibit following characteristics or benefits: larger packing density, enhanced mechanical properties, easy manipulation due to string backbone, etc.

The present disclosure also provides a method of preparing the MTAM having the multiple layers of fibers which are aligned in the z-direction, comprising in a shell-fluid coxial electrospinning process, using a shell solution comprising about 15 wt % to about 25 wt % polymeric solution under a flow rate large than 10 mL/hr and a voltage of about 8 kV to about 11 kV, while maintaining a spinneret height of about 1-3 cm. In one embodiment, the polymeric solution is PSF/PVP solved in a co-solvent of THF and DMAC. The preparation of the MTMA-dl-al with multiple layer structures comprises in a shell-fluid coxial electrospinning process, using a shell solution comprising about 15 wt/o to about 25 wt % polymeric solution under a flow rate large than 10 mL/hr and a voltage of about 8 kV to about 11 kV. In one embodiment, the polymeric solution is PSF/PVP solved in a co-solvent of THF and DMAC.

These types of MTAMs have high surface-to-volume ratio and can be targeted for absorbance-based applications such as endotoxin removal, CTC capture as a metastasis prevention/diagnosis device. Additionally, these systems can also be applied in applications in the rapid bio sensing of disease.

The numbers of fibers of the MTAMs pack together and the orientation angle of the fibers in the fiber assembly represent the degrees of packing and alignment, respectively. A larger fiber number means greater packing density, whereas a smaller orientation angle shows the degree of electrospun fiber alignment.

In another aspect, the present disclosure provides a pocket enclosing any microtube array membrane (MTAM) noted above. The techniques for producing a pocket which is bioavailable can be conventional in the art. Examples of materials for producing a pocket include, but are not limited to polysulfone, polylactic acid and majority of the solvent soluble polymers.

The pocket enclosing the MTMAs as claimed may be useful in medical, pharmaceutical or biological applications. For example, the pocket may be used for drug screening, endotoxin removal, filtration, separation, etc.

Without being bound to the theory, Hairy MTMA-multilayer may exhibit following characteristics or benefits: larger surface area, enhanced cell attachment via nanotopography eliciting pro-attachment proteins, larger packing density, etc.

The examples and embodiments disclosed herein are to be construed as merely illustrative and exemplary, and not a limitation of the scope of the present disclosure in any way. It will be apparent to those having skill with the aid of the present disclosure in the art that changes may be made to the details of the above-described embodiments without departing from the underlying principles of the disclosure herein. It is intended that the scope of the invention be defined by the claims appended hereto and their equivalents.

EXAMPLE

Example 1 Hairy Microtube Array Membrane (MTMA-Hairy)

Materials used as core solution in fabrication of the hollow fiber assembly were poly-L-lactic acid (PLLA; Mw=140 KDa, Japan), poly-ethylene glycol (PEG; Mw=35000 Da, Sigma-Aldrich), poly-ethylene oxide (PEO; Mw=900,000 Da, Sigma-Aldrich), and solvent of Dichloromethane (DCM; Mallinckrodt, USA), N,N-Dimethyl formamide (DMF) were purchased from Sigma-Aldrich, Inc. (St. Louis, MO).

The outer shell solution is a 15% poly(lactic acid) (PLLA) solution in a solvent mixture of dichloromethane (DCM) and N,N-Dimethyl formamide (DMF) at ratio of 9:1. The inner core solution is prepared as follows: first, dissolving PLLA in a solvent mixture of DCM:DMF at a ratio of 8:2 to form 15 wt. % PLLA solution; then, introducing 1.3 g of Polyethylene oxide (PEO) and 1.3 g of Polyethylene glycol (PEG) into the PLLA solution. Upon completely dissolving, 20 mL of acetone was added to the mixture and sonicated for at least 3 hours. The electrospinning parameters for obtaining the PLLA/PLLA-PEG-PEO shell-core fibers were as follows: 7.2 kV applied voltage at a maximum amperage of 200 μA, 5 mL/h inner flow rate, 6 mL/h outer flow rate, collection speed of the drum collector at 100 rpm.

FIG. 1 shows the SEM images of the MTMA-h thus obtained, with different magnification rates.

Example 2 Hairy Microtube Array Membrane (MTMA-Hairy)

The fabrication parameters are similar to that outlined in Example 1. The formulation of the core solution consists of 5 wt % PLLA dissolved in a solvent mixture of DCM:DMF at a ratio of 8:2. Upon completely dissolving, 1 mL of polyethylene glycol (PEG 40; $M_w$: 40 KD. PEG 40 functions as a surfactant and was added to the mixture and stirred for 3 hours. The shell solution consists of 15 wt % PLLA dissolved in a co-solvent of DCM:DMF at a ratio of 8:2 and dissolved until homogenous.

Figure 2:
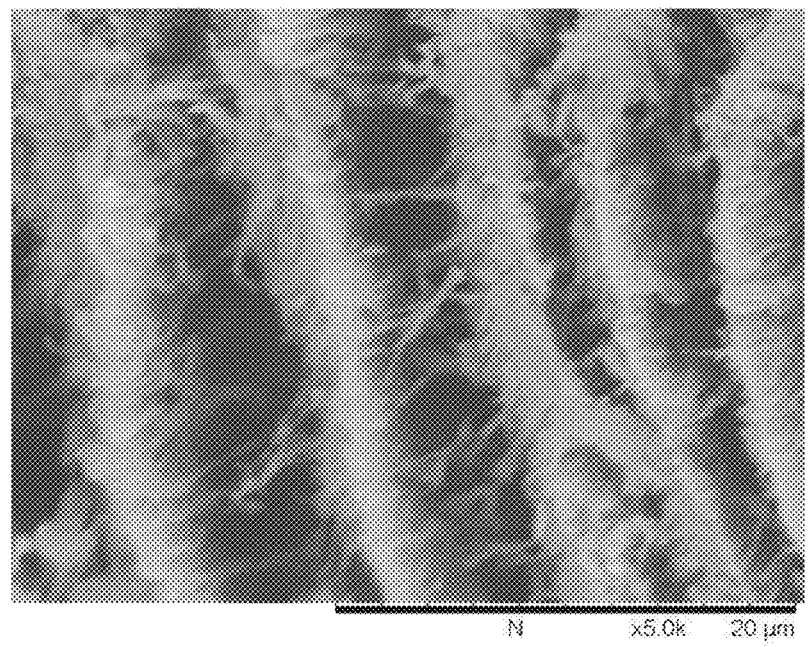
FIG. 2 shows SEM images (transverse view) of embodiments of MTAM-p (having sponge-like fibers).
Figure 2:
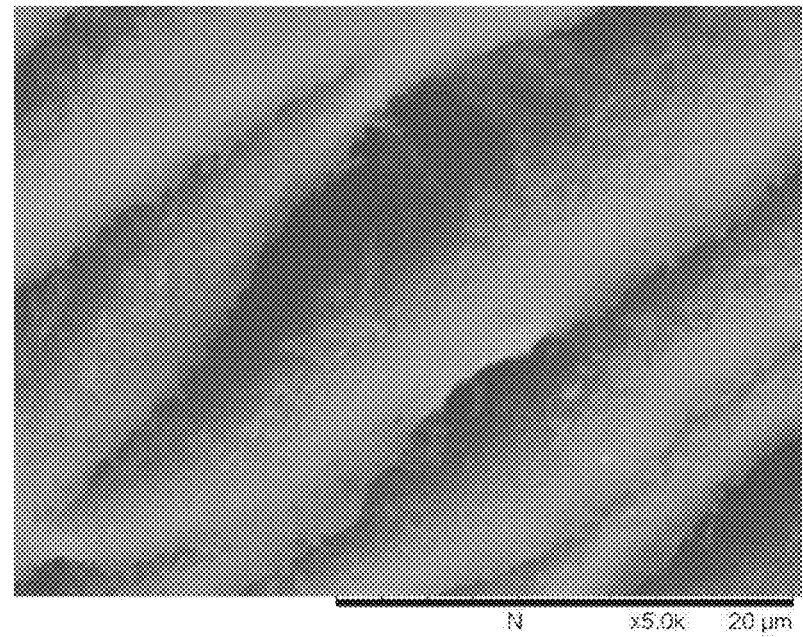

FIG. 2 shows the SEM images of the MTMA-p thus obtained, with different magnification rates. Highly fine and ultra-porous sponge-like structures were clearly visible in the inner surfaces of the MTAM-Hairy.

Example 3 Multi-Layered Microtube Array Membrane

Figure 3:
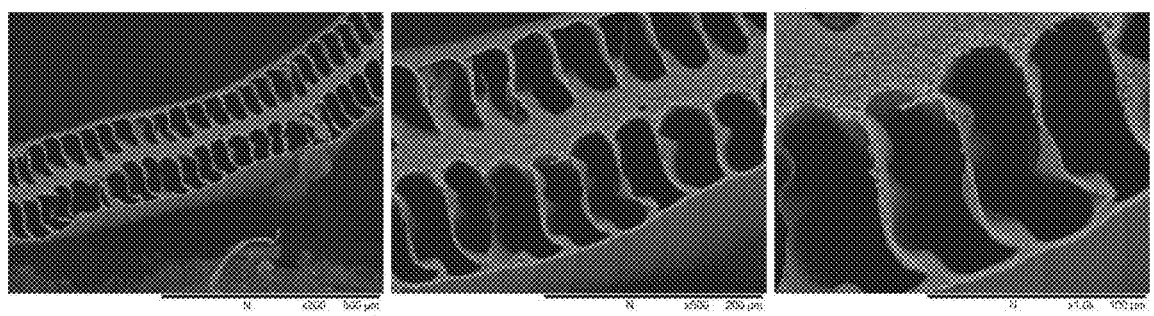
FIGS. 3(a) and 3(b) show SEM images (transverse view/top view) of embodiments of MTAM-dl (having a double-layered configuration of fibers)
Figure 3:
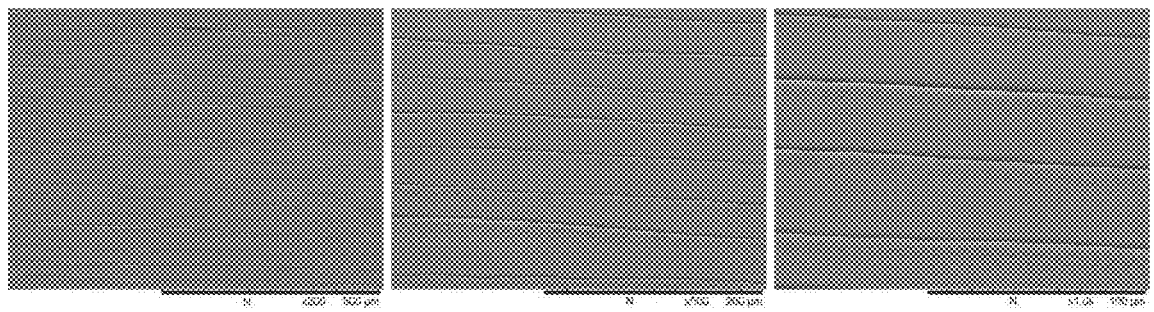
Figure 4:
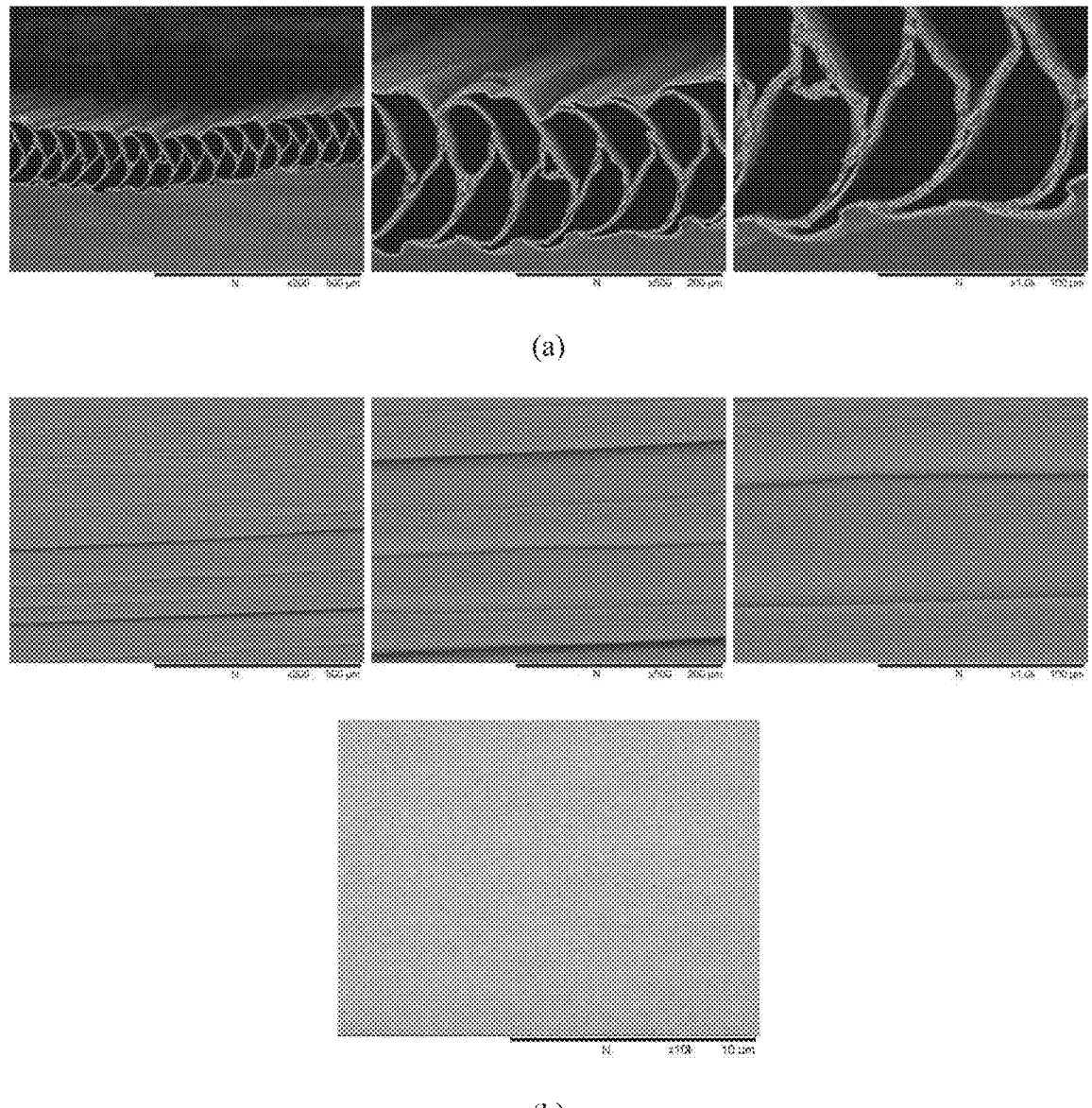
FIGS. 4(a) and 4(b) show SEM images (transverse view/top view) of embodiments of MTAM-dl-al (having an alternating configuration of fibers).
Figure 5:
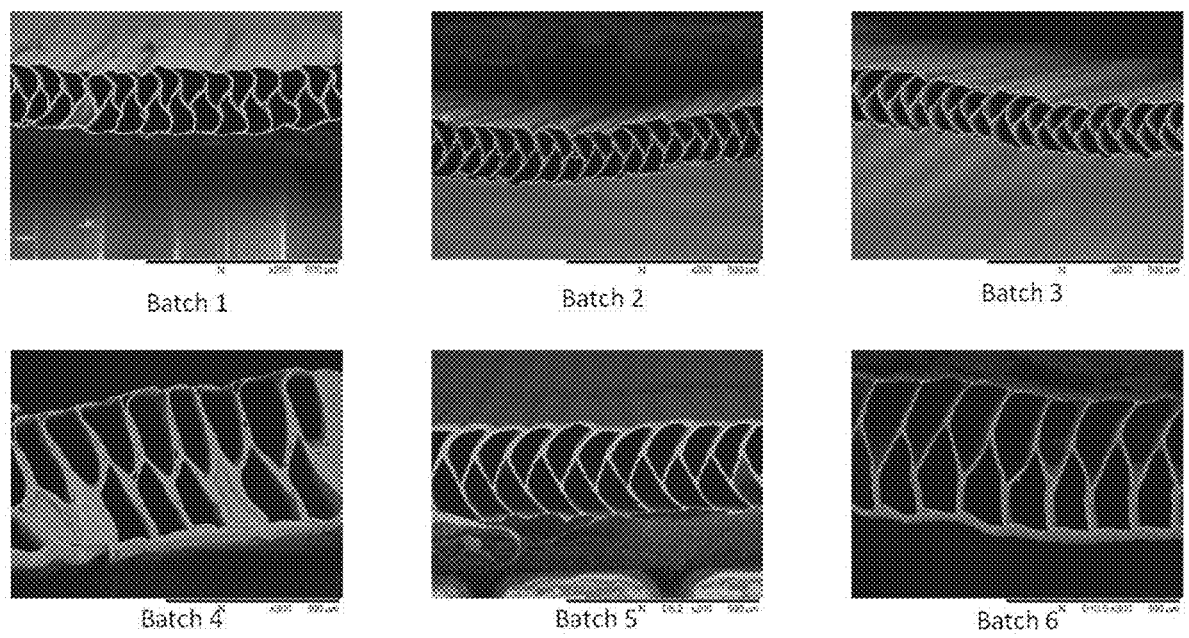
FIG. 5 illustrates excellent reproducibility of MTAM-dl-al.

The parameters for producing electrospun MTAMs were modified. A shell solution contains 20 wt % polysulfone/ polyvinylpyrrolidone (PSF/PVP) in a solvent mixture of THF/DMAC in under high flow rate conditions (>10 mL/hr) under the voltage of 8 kV-11 kV. The collector was set at a rotation speed of 50-60 rpm. FIG. 3 shows SEM images of MTMA having two layers, i.e., MTMA-dl (FIG. 3(a): transverse view; FIG. 3(b) top view). FIG. 4 shows SEM images MTMA having two layers arranged alternatively, i.e., MTMA-dl-al (FIG. 4(a): transverse view; FIG. 4(b) top view). FIG. 5 illustrates reproducibility of MTMA-dl-al prepared in different batches by the same or different producers.

Example 4 Multi-Layered Microtube Array Membrane with Hairy Structure

Figure 6:
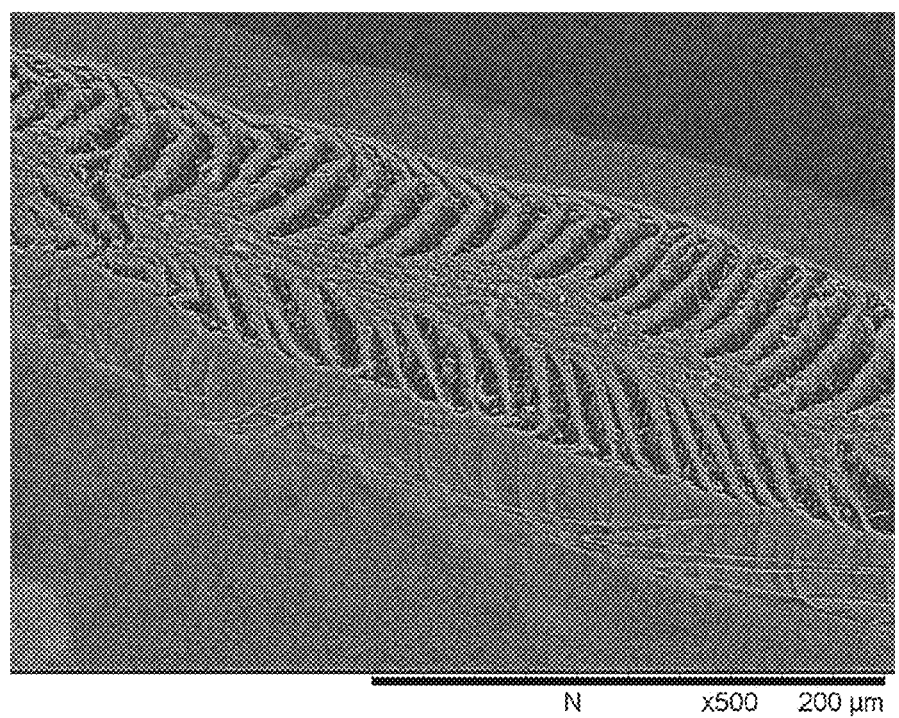
FIG. 6 shows an SEM image of embodiments of MTAM-dl-h (having hairy extension parts within double-layered configuration of fibers).

The parameters for producing electrospun MTAMs were modified to prepare MTAMs with an alternating layered structure. A shell solution contains 20 wt % polysulfone/ polyvinylpyrrolidone (PSF/PVP) in a solvent mixture of THF/DMAC in under high flow rate conditions (>10 mL/hr) under the voltage of 8 kV-11 kV. The collector was set at a rotation speed of 50-60 rpm. FIG. 6 shows SEM images of MTMA having two layers with hairy structures on the surface of the wall of the microtubes, i.e., MTMA-dl-h.

Example 5 Cell Viability Tests

In tissue engineering, one key component which dictates the cell adhesion is the presence of nanotopography which contributes to the initial protein adsorption followed by the actual adhesion of cells. When using MTMA of the invention in anti-cancer drug screening applications, a key challenge is to ensure that there is a significant difference between the control groups and the groups administered with the desired anti-cancer drugs. Therefore, it is critical that the initial tumorgenicity is increased. This can be achieved by utilizing MTAM-h or other MTMAs provided in the subject application as they will provide nanotopography which is critical for the adhesion and proliferation of cancer cells.

Figure 7:
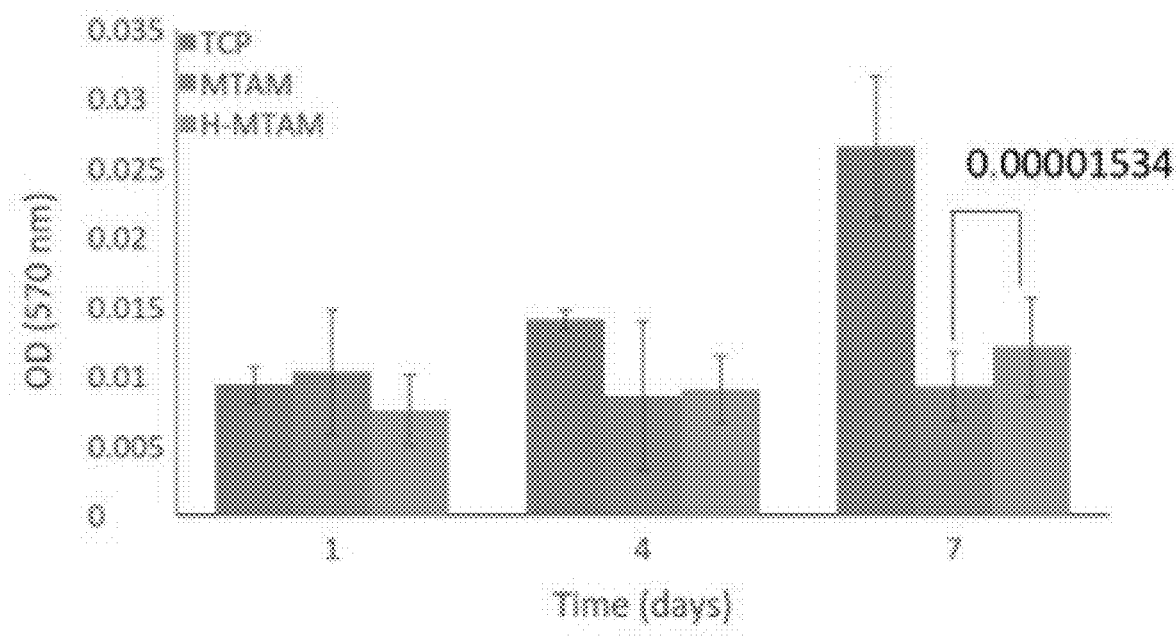
FIG. 7 shows the cell viability on TCP, MTAM and MTAM-h.

In this example, lung cancer cell line A549 is utilized as a model. The cells were cultured in RPMI 1640 medium for 24 hours. Next, $1 \times 10^4$ cells present in a 10 µL droplet were transferred onto a sheet of sterile parafilm and siphoned into the lumens of the MTAM (with no surface nanotopography) and MTAM-h of the invention. The ends were folded over to seal the lumens of these MTAMs and cultured in RPMI 1640 medium at 37° C. under an atmospheric condition of 5% carbon dioxide. At day 1, 4 ad 7, samples were retrieved and MTT assay was carried out to determine the cell viability. The results are shown in FIG. 7.

Statistical analysis revealed that there was a significant difference ($p<0.005$) in cell viability of A549 cells cultured in MTAM with no surface nanotopography and MTAM-h of the invention; strongly suggesting that the nanotopography present in the MTAM-h played a key role in increasing the overall cellular viability of the A549 cells.

Example 6 Endotoxin Removal Tests

In this example, MTAM-h is used in the application of endotoxin removal. Experiments for evaluating the absorption capacity of MTAM-h of the invention and MTAMs with no nanotopography have been conducted.

The procedures involve the acetic acid plasma treatment of the PLLA-MTAM surface of both MTAM and MTAM-h. This treatment significantly reduces the water contact angle which indicated an increase in hydrophilicity. Additionally, the acetic acid plasma treatment allows for more hydroxyl ending being present on the surface of the PLLA-MTAMs thereby allowing for more immobilization of Polymyxin B (via UV rays), which is an antibiotic commonly used in commercially available products for endotoxin removal such as Toraymyxin. Both types of MTAMs were then transferred into two different solutions containing endotoxin at a concentration of 100 EU/mL. After 60 minutes, the surrounding solution was retrieved independently and tested for evaluating the endotoxin levels.

Figure 8:
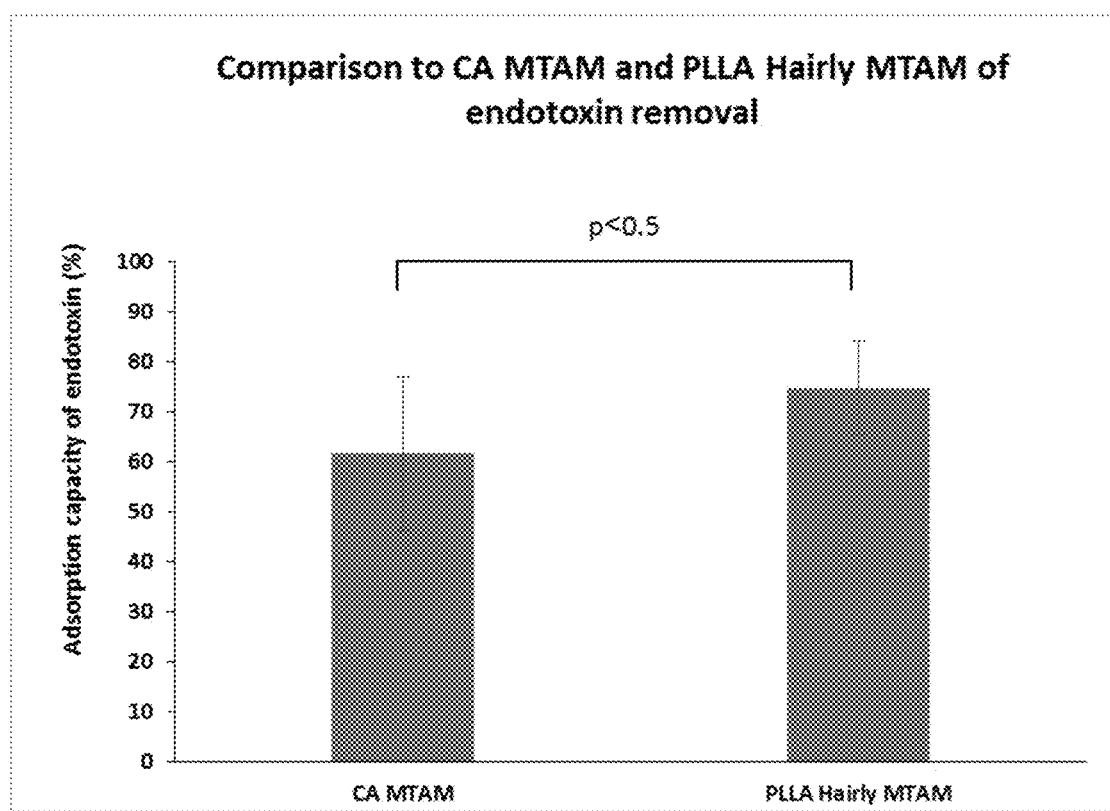
FIG. 8 shows the absorption capacity of endotoxin of MTMA and MTMA-h having immobilized antibiotics on the surface thereof.

The results indicated that the MTAM-h registered a significantly higher absorption capacity of about 13% when compared with the MTAMs with no surface nanotopography (see, FIG. 8). Additionally, statistical analysis revealed that such difference is significant. Without being bound to the theory, the nanotopography/nanostructure such as a hair-like structure significantly increases the overall available surface area due to increased surface area, which allows for more sites for the adsorption of Polymyxin B. This result translates to a greater absorption capacity of endotoxin levels.

Another example is provided for illustrating using MTAM-al in the application of endotoxin removal. Experiments for evaluating the absorption capacity of MTAM-h of the invention and Toraymyxin™, a conventional product for endotoxin removal, have been conducted.

Figure 9:
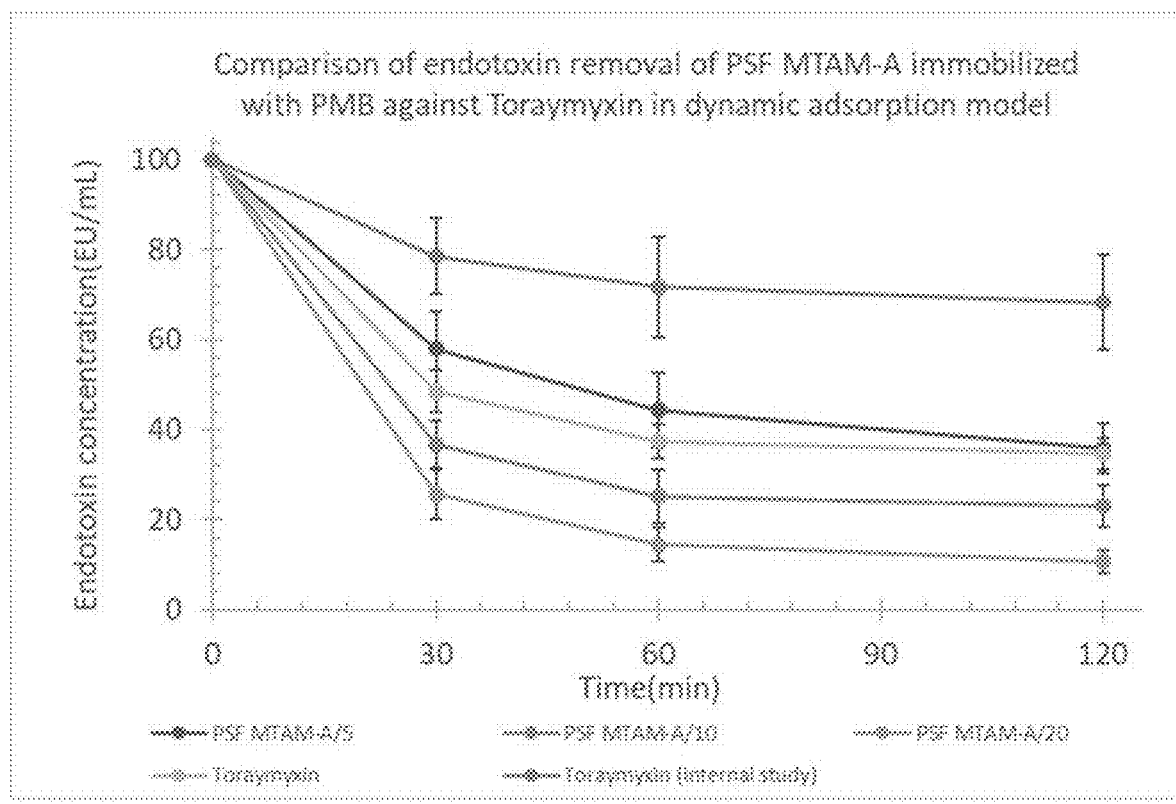
FIG. 9 shows the absorption capacity of endotoxin of MTMA-al having immobilized antibiotics on the surface thereof and Toraymyxin™.

The results indicated that the MTAM-al registered comparable and even a significantly higher absorption capacity when compared with the Toraymyxin™. Additionally, statistical analysis revealed that such difference is significant. Without being bound to the theory, the claimed MTAM-al has a larger surface area than a single layered MTAM (e.g., 1.3-fold increase in one example), which allows for more sites for the adsorption of Polymyxin B. The unique structure of the claimed MTAM-al also allows the absorption capacity to be higher than that can be provided by the conventional material, Toraymyxin™ (see, FIG. 9)

What is claimed is:

1. A hollow electrospun fiber assembly, comprising multiple fibers having nanoscale hair-like structures extended from an inner surface thereof, wherein the hair-like structures consist of the material of the fibers and have a length ranging from 100 nm to 1 µm and an aspect ratio of up to 20:1, and wherein the surface coverage of the hair-like structure is about 10% to about 80%.

2. The hollow electrospun fiber assembly of claim 1, wherein the fibers have pores on the surface, wherein the pores have a size ranging from 5 nm to 1 µm.

3. The hollow electrospun fiber assembly of claim 1, wherein the fibers are composed of a polymer selected from a group consisting of ethylene oxide, polyethylene oxide (PEO), ethylene glycol, polyethylene glycol (PEG), poly (lactic acid) (PLA), poly (glycolic acid) (PGA), nylon, polyesters, polyamides, poly (amino acids), polyimides, polyethers, polyketones, polyurethanes, polycaprolactones, polyacrylonitriles, polyaramides, conjugated polymers, poly (2-methoxy, 5 ethyl (2' hexyloxy) para-phenylene vinylene) (MEH-PPV), polyphenylenevinylenes, polyarylene-vinylenes, polythienolene-vinylenes, polypyrrolo-vinylenes, polyheteroarylene-vinylenes, polyanilines, polyphenylenes, polyarylenes, polythiophenes, polypyrroles, polyheteroarylenes, polyphenylene-ethynylenes, polyarylene-ethynylenes, polythieno-ethynylenes, polyheteroarylene-ethynylenes, and mixtures thereof.

4. The hollow electrospun fiber assembly of claim 1, wherein the fiber has a core-shell structure, wherein the core is composed of a mixture of PLA, PEO and PEG.

5. The hollow electrospun fiber assembly of claim 1, wherein the length-to-diameter (outer) ratio (L/d) of a fiber is larger than about 20.

6. A microtube array membrane (MTAM) comprising one or more layers of hollow electrospinning fiber assembly of claim 1.

7. The MTAM of claim 6, which comprises at least two layers of the fiber assembly.

8. The MTAM of claim 6, which has a structure wherein the layers of fibers are alternatively or perpendicularly arranged.

9. A pocket enclosing the hollow electrospun fiber assembly of claim 1.

10. A pocket enclosing the MTAM of claim 6.

11. A hollow electrospun fiber assembly of claim 1 for uses in drug screening, matrix form cell cultivation, fermentation, tissue engineering, drug screening, or filtration.

12. A MTAM of claim 6 for uses in drug screening, matrix form cell cultivation, fermentation, tissue engineering, drug screening, or filtration.

13. A hollow electrospun fiber assembly, comprising multiple fibers having nanoscale hair-like structures extended from an inner surface thereof, wherein the fiber has a core-shell structure, and the core is composed of a mixture of PLA, PEO, and PEG.

14. A pocket enclosing the hollow electrospun fiber assembly of claim 13.

15. A pocket enclosing a microtube array membrane (MTAM), wherein the MTAM comprises one or more layers of hollow electrospinning fiber assembly of claim 13.

16. A hollow electrospun fiber assembly of claim 13 for uses in drug screening, matrix form cell cultivation, fermentation, tissue engineering, drug screening, or filtration.

17. A microtube array membrane (MTAM) for uses in drug screening, matrix form cell cultivation, fermentation, tissue engineering, drug screening, or filtration, wherein the MTAM comprises one or more layers of hollow electrospinning fiber assembly of claim 13.

* * * * *